United States Patent
Boutoussov et al.

(10) Patent No.: US 7,421,186 B2
(45) Date of Patent: Sep. 2, 2008

(54) MODIFIED-OUTPUT FIBER OPTIC TIPS

(75) Inventors: Dmitri Boutoussov, Dana Point, CA (US); John Hendy, Grants Pass, OR (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

(21) Appl. No.: 11/800,184

(22) Filed: May 3, 2007

(65) Prior Publication Data

US 2007/0263975 A1    Nov. 15, 2007

Related U.S. Application Data

(60) Provisional application No. 60/898,022, filed on Jan. 26, 2007.

(51) Int. Cl.
  *G02B 6/26* (2006.01)
  *G02B 6/02* (2006.01)
  *A61B 18/18* (2006.01)

(52) U.S. Cl. .............................. 385/146; 385/43; 606/16

(58) Field of Classification Search ........................ None
See application file for complete search history.

(56) References Cited

U.S. PATENT DOCUMENTS

| | | | |
|---|---|---|---|
| 5,188,634 A * | 2/1993 | Hussein et al. ................. | 606/14 |
| 5,257,991 A | 11/1993 | Fletcher et al. | |
| 5,303,324 A | 4/1994 | Lundahl | |
| 5,428,699 A | 6/1995 | Pon | |
| 5,497,441 A | 3/1996 | Croitoru et al. | |
| 5,772,657 A | 6/1998 | Hmelar et al. | |
| 5,785,645 A * | 7/1998 | Scheller ...................... | 600/171 |
| 5,836,941 A | 11/1998 | Yoshihara et al. | |
| 5,953,477 A | 9/1999 | Wach et al. | |
| 6,129,721 A | 10/2000 | Kataoka et al. | |
| 6,332,053 B1 * | 12/2001 | Irie et al. .................... | 385/123 |
| 6,620,153 B2 | 9/2003 | Mueller et al. | |
| 6,748,137 B2 * | 6/2004 | Wolak et al. .................. | 385/33 |
| 6,802,838 B2 | 10/2004 | Loeb et al. | |
| 2005/0256517 A1 * | 11/2005 | Boutoussov ................. | 606/16 |

OTHER PUBLICATIONS

International Search Report, May 25, 2006, PCT/US05/00851.

* cited by examiner

*Primary Examiner*—Hemang Sanghavi
*Assistant Examiner*—Omar Rojas
(74) *Attorney, Agent, or Firm*—Stout, Uxa, Buyan & Mullins, LLP

(57) ABSTRACT

A laser handpiece is disclosed, including a shaped fiber optic tip having a side-firing output end with a double bevel-cut shape. The shaped fiber optic tip can be configured to side-fire laser energy in a direction away from a laser handpiece and toward sidewalls of a treatment or target site.

33 Claims, 11 Drawing Sheets

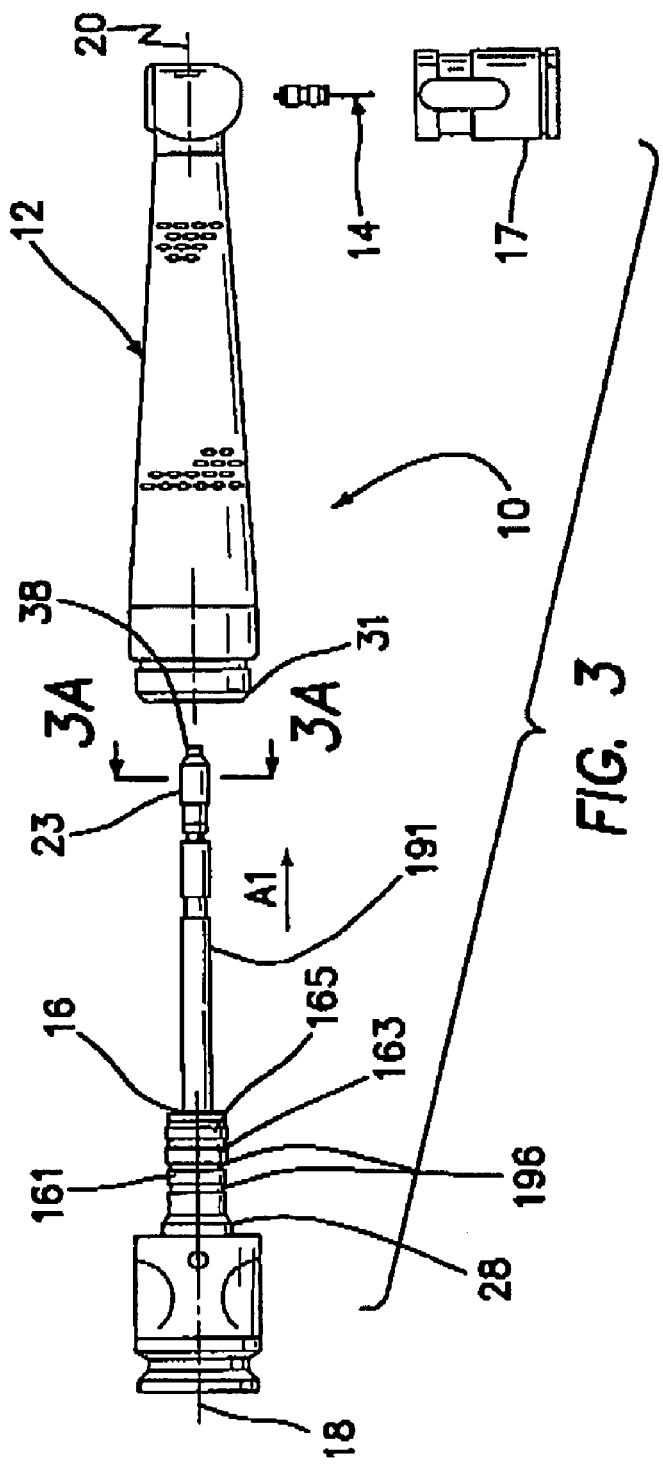

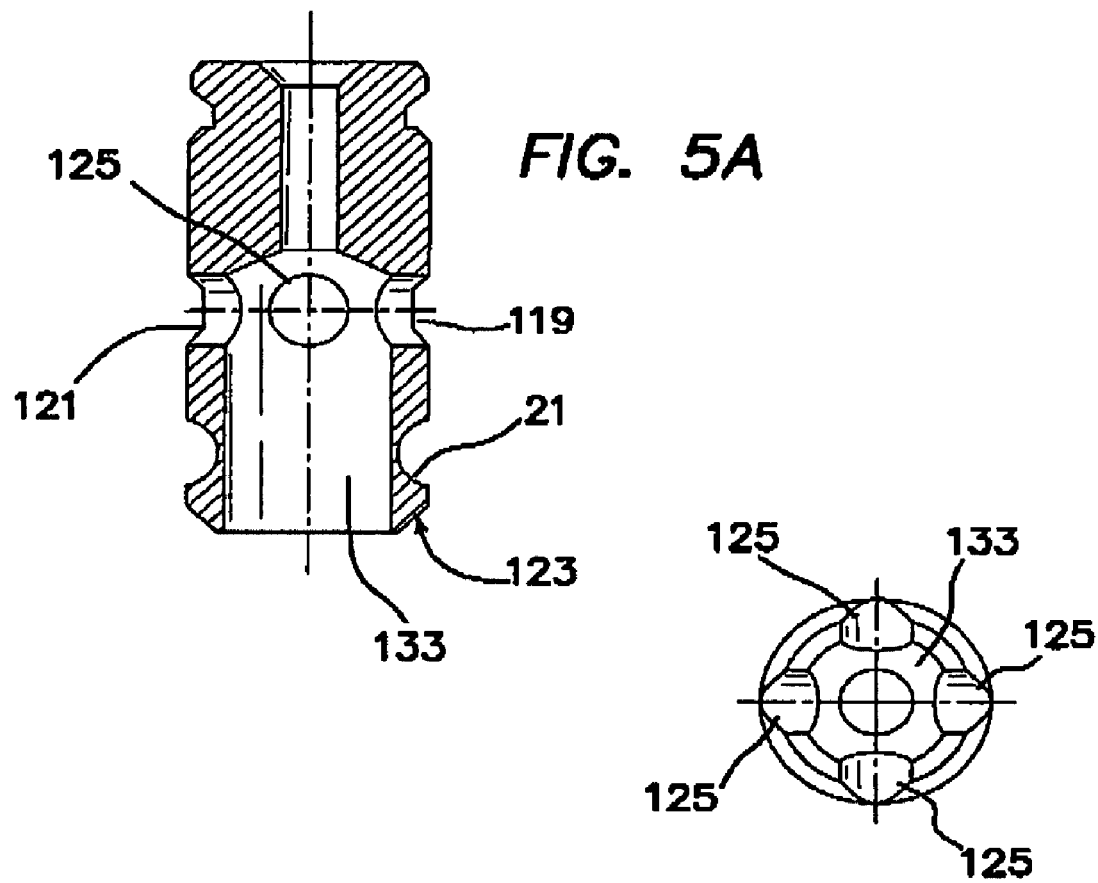
FIG. 5A
FIG. 5B
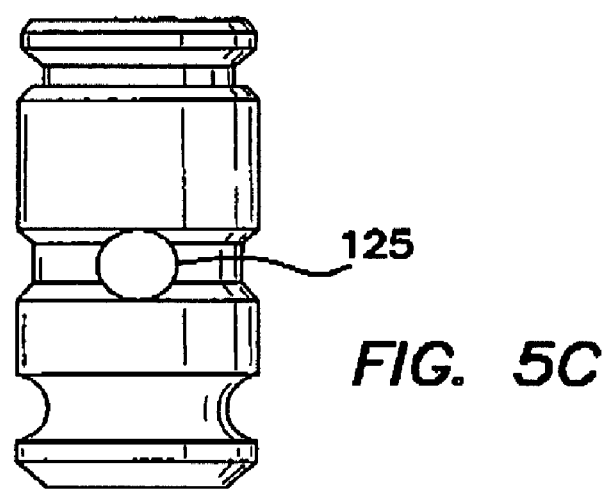
FIG. 5C

MODIFIED-OUTPUT FIBER OPTIC TIPS

CROSS-REFERENCE TO RELATED APPLICATIONS

The application claims the benefit of U.S. Application No. 60/898,022, filed on Jan. 26, 2007. This application is related to U.S. application Ser. No. 11/033,441, filed on Jan. 10, 2005, the entire contents of both which are incorporated herein by reference.

BACKGROUND OF THE INVENTION

1. Field of the Invention

The present invention relates generally to medical devices and, more particularly, to fiber optic tips for delivering electromagnetic radiation.

2. Description of the Related Art

Fiber optics have existed in the prior art for delivering electromagnetic radiation. Radiation delivery systems are typically used to transport electromagnetic radiation from electromagnetic energy sources to treatment sites. One common radiation delivery system can comprise a cylindrically-shaped fiber optic tip from which electromagnetic radiation is emitted in a direction toward the treatment site.

In certain applications, radiation delivery systems can be engineered to generate predetermined beam shapes and spatial energy distributions. The energy distribution of a simple delivery system, comprising a fiber optic tip, can be described as having a circular illumination area, with a so-called Gaussian distribution of beam intensities being spatially distributed within the output beam pattern or illuminated area. For instance, the output beam pattern from a fiber optic tip can comprise a central high-intensity area or "hot spot" surrounded by peripheral areas of lower intensity.

Regarding energy distributions, some beam profiling applications can require or would be optimized with radiation delivery systems capable of generating illumination distributions that vary across parts or all of the illumination area surrounding the output of the radiation delivery system. Moreover, it may also be desirable to generate non-circular illumination areas, or to generate electromagnetic radiation having predetermined energy distributions across a non-planar illumination area. Use of laser radiation having a relatively uniform power distribution over a particularly shaped area can be a practical task for multiple medical applications.

SUMMARY OF THE INVENTION

The present invention provides optical arrangements and relatively compact medical laser instruments to deliver electromagnetic radiation to treatment sites with power distributions that may vary in a non-Gaussian distribution fashion, compared to cylindrical output fibers, across parts or all of the illumination area surrounding the output waveguide. The illumination areas may comprise non-circular or curved surfaces, such as cavities, in which case substantial output power densities can be concentrated on sidewalls of the illumination areas. The electromagnetic radiation can comprise laser radiation, and the treatment site can comprise tissue to be treated.

The various embodiments of the present invention may include or address one or more of the following objectives. One objective is to provide a fiber optic tip having a shaped fiber optic output end (i.e., a fiber optic output end not consisting only of a planar surface orthogonal to the fiber optic axis) for delivery of electromagnetic radiation, wherein electromagnetic radiation exiting the fiber optic output end is not concentrated along the fiber optic axis. Another objective is to provide a fiber optic output end having an emission characteristic whereby electromagnetic radiation exiting the fiber optic output end is relatively weak along the fiber optic axis. Yet another object is to provide a fiber optic output end wherein all waveguide modes experience a majority or total internal reflection on a first surface of the fiber optic output end and go out through an opposite surface of the fiber optic output end. Still another objective is to provide a apparatus for directing laser energy and optionally fluid to different target sites through different reflections within a fiber conduit and from the fiber conduit to the output end or sites, wherein different energy distributions can be provided to different treatment surfaces surrounding or in a vicinity to the fiber conduit at the same time.

While the apparatus and method have or will be described for the sake of grammatical fluidity with functional explanations, it is to be expressly understood that terms in the claims, unless expressly formulated under 35 USC 112, are not to be construed as necessarily limited in any way by the construction of "means" or "steps" limitations, but are to be accorded the full scope of the meaning and equivalents of the definition provided by such claims under the judicial doctrine of equivalents, and in the case where terms in the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one of ordinary skill in the art. For purposes of summarizing the present invention, certain aspects, advantages and novel features of the present invention have been described herein. Of course, it is to be understood that not necessarily all such aspects, advantages or features will be embodied in any particular embodiment of the present invention. Additional advantages and aspects of the present invention are apparent in the following detailed description and claims.

BRIEF DESCRIPTION OF THE FIGURES

FIG. 3 is a side elevation view of the rotating hand piece in a partially disassembled state;

FIGS. 3a-6 are other views of the structure;

DETAILED DESCRIPTION OF THE PRESENT INVENTION

Figure 1:
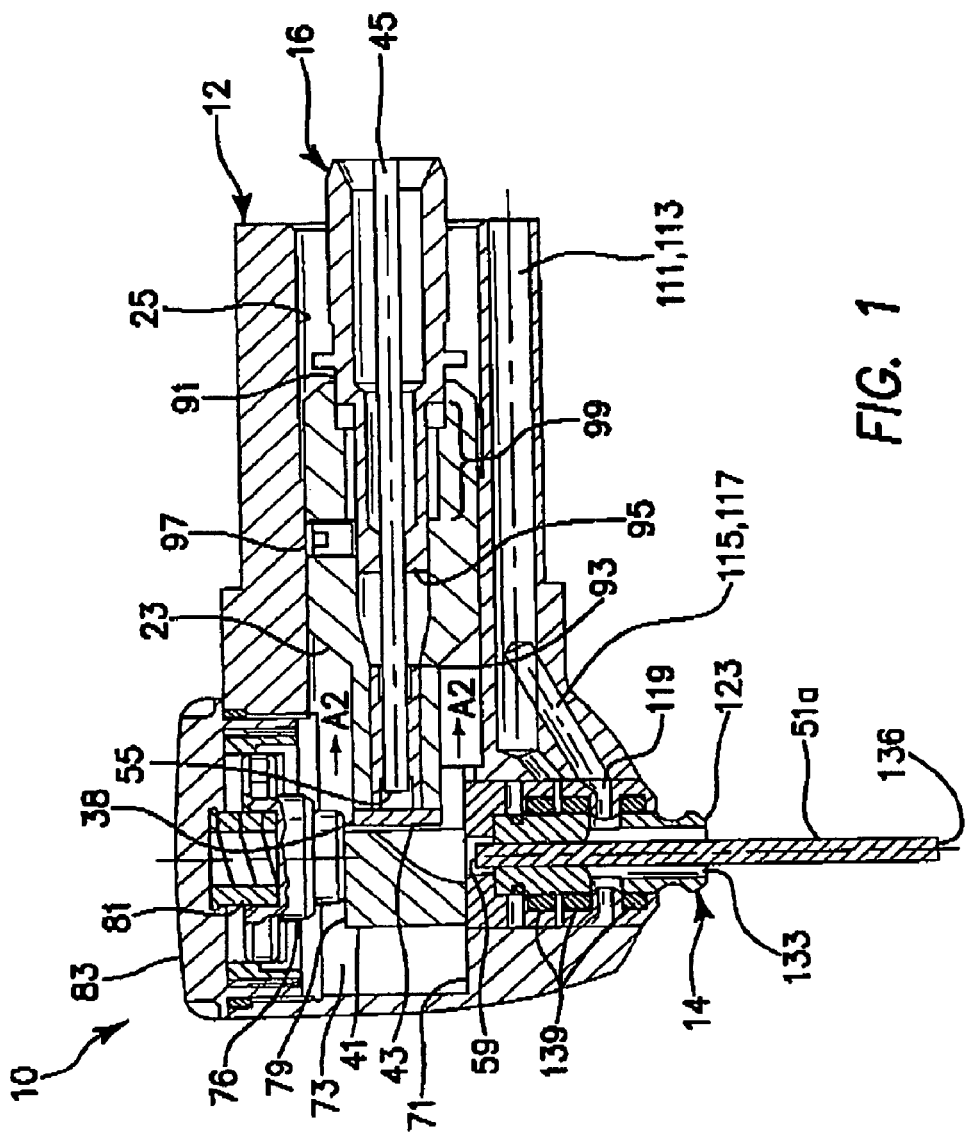
FIG. 1 is a cross-sectional view of a rotating handpiece.

Reference will now be made in detail to certain embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

Referring more particularly to the drawings, FIG. 1 illustrates a cross sectional view of the rotating handpiece 10. The rotating handpiece comprises a handpiece head 12, a fiber tip fluid output device 14, and a removable trunk fiber assembly 16. These components can be seen in a partially disassembled state in FIG. 3, wherein the axis 18 of the removable trunk fiber assembly 16 is aligned with the axis 20 of the handpiece head 12 for insertion into the handpiece head 12. Once the axis 18 of the removable fiber assembly 16 is aligned with the axis 20 of the handpiece 12, the removable trunk fiber assembly 16 is moved in the direction of the arrow A1 into the handpiece head 12, while the axes 18 and 20 are maintained in approximate alignment. The contacting surface of the outer surface of the chuck 23 engages the inner surface 25 of the rotating handpiece 10, to thereby ensure alignment of the axis 18 of the removable trunk fiber assembly 16 and the axis 20 of the handpiece head 12. As the removable trunk fiber assembly 16 is inserted further in the direction A1 into the handpiece 12, the abutting surface 28 engages with a corresponding abutting surface (not shown) within the collar 31 of the handpiece head 12. The corresponding abutting surface 28 can be constructed to snap with the abutting surface 31, as the removable trunk fiber assembly 16 is fully inserted into the handpiece head 12. Any type of locking engagement between the abutting surface 28 and a corresponding abutting surface within the collar 31, as known in the art, may be used to ensure that the removable trunk fiber assembly 16 is always inserted the same distance into the handpiece head 12. As shown in FIG. 1, the distal tip 38 of the removable trunk fiber assembly 16 is brought into close proximity with the parabolic mirror 41. In the illustrated embodiment, the distal tip 38 of the removable trunk fiber assembly 16 comprises a window 43 for protecting the trunk fiber optic 45 from contaminants, such as water. In the alternative embodiment shown in FIG. 2, the distal tip 38a is not protected with a window. As shown in FIG. 1, the fiber tip 51 of the fiber tip fluid output device 14 is also accurately placed in close proximity to the parabolic mirror 41. A loading tool 17 can be used to assist in the placement of the fiber tip fluid output device 14 into the handpiece head 12, as discussed below with reference to FIGS. 5 and 7-9. Electromagnetic radiation exiting from the output end 55 of the trunk fiber optic 45 is collected by the parabolic mirror 41 and, subsequently, reflected and focused onto the input end 59 of the fiber tip 51.

Figure 4A:
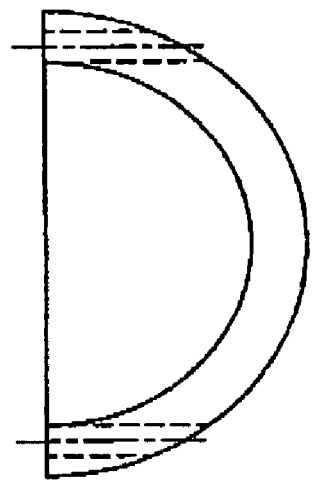
Figure 4B:
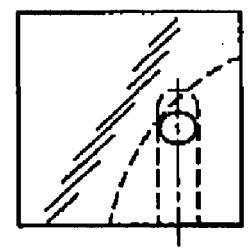
Figure 4C:
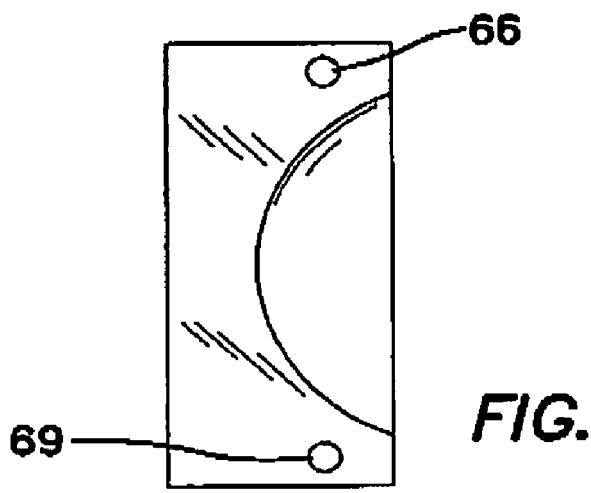

In one embodiment, the electromagnetic radiation exiting from the output end 55 of the trunk fiber optic 45 comprises a wavelength on the order of 3 microns. In other embodiments, electromagnetic radiation can be supplied at wavelengths from about 0.4 micron to about 11 microns, and in typical embodiments from about 0.4 micron to about 3 microns, from a light source such as a plasma arc lamp, a LED, or a laser having a continuous wave (CW) or pulsed mode of operation. The material of the parabolic mirror 41 is selected to provide an efficient reflection and focusing into the input end 59. As presently embodied, the electromagnetic radiation is generated from an Er:YSGG laser, and the material of the parabolic mirror 41 comprises a gold plating to provide reflectivity of approximately 99.9 percent. Other materials may be selected in accordance with design parameters. Other reflective surfaces and materials for the parabolic mirror 41 may be selected, in accordance with the laser being used and the desired efficiency of reflection. For example, if a lower reflectivity is selected, then additional cooling may be needed for the parabolic mirror 41 (such as a greater flow rate of cooled and/or filtered air across the surface of the parabolic mirror 41). FIGS. 4a, 4b and 4c illustrate various views of the parabolic mirrors 41 of the presently illustrated embodiment. The flat surface of the parabolic mirror 41, which is closest to the fiber tip 51, can be provided with two recessed areas 66 and 69. These two recessed areas mate with corresponding protrusions (not shown) on the floor 71 of the internal chamber 73 of the handpiece head 12. A spring loaded plunger 76 presses against the upper surface 79 of the parabolic mirror 41 under the pressure of the spring 81. A screw cap 83 holds the spring 81 against the spring loaded plunger 76. The combination of the spring loaded plunger 76, the recessed areas 66,69 of the parabolic mirror 41, and the corresponding protrusions on the floor 71, together, accurately align the parabolic mirror 41 for efficient coupling of electromagnetic radiation between the output end 55 of the trunk fiber optic 45 and the input end 59 of the fiber tip 51. In modified embodiments, either or both of the output end 55 of the trunk fiber optic 45 and the input end 59 of the fiber tip 51 is/are provided with an anti-reflective coating. Although it may be preferred in certain implementations to have the trunk fiber optic 45 perfectly aligned in relation to the parabolic mirror 41 and the fiber tip 51, the alignment between these three elements is seldomly perfect. In the presently illustrated embodiment, the misalignment of the axis of the trunk fiber optic 45 and the axis of the fiber tip 51 is within plus or minus 1 percent error.

In a modified embodiment, a pentaprism (five-sided prism) is used instead of the parabolic mirror 41 for coupling the trunk fiber optic 45 to the fiber tip 51. In addition to slight misalignment of the axis of the trunk fiber optic 45, slight imperfections on the output end 55 of the trunk fiber optic 45 may also be present. The parabolic mirror 41 corrects for both of these slight errors, by collecting the electromagnetic radiation from the output end 55 of the front fiber optic 45 and, subsequently, focusing the electromagnetic radiation into the input end 55 of the fiber tip 51.

The parabolic mirror 41 may also comprise molypdium, in an exemplary embodiment. The clamp assembly 91 operates to firmly grip and hold the trunk fiber optic 45. In the presently illustrated embodiment, the clamp assembly 91 is provided with at least one slit, which extends from the distal end 93 of the clamp assembly 91 to a region 95 just distal of the set screw 97. As presently embodied, the at least one slit extending from the distal end 93 to the region 95 just distal of the set screw 97 comprises two slits, which are adapted to allow the clamp assembly 91 to be compressed by the chuck 23 onto the trunk fiber optic 45. The chuck 23 thus presses against the portion of the clamp assembly 91, wherein the portion is defined between the distal end 93 and the region 95, to thereby have the clamp assembly 91 squeeze and hold the trunk fiber optic 45 in place. In the presently illustrated embodiment, the set screw 97 is used to hold the chuck 23 in place and prevent rotation thereof. In the illustrated embodiment, the outer surface of the clamp assembly 91 is provided with threads 99 for engaging with corresponding threads on the inner surface of the chuck 23. In the illustrated embodiment, the chuck 23 is screwed onto the threads of the clamp assembly 91, before the removable trunk fiber assembly 16 is inserted into the handpiece 12. The chuck 23 is screwed onto the clamp assembly 91 to a predetermined tightness, and then the set screw 97 is secured thereto to securely hold the chuck 23 to the clamp assembly 91. Subsequently, the removable trunk fiber assembly 16 is inserted and secured into the handpiece head 12.

Referring to FIGS. 5 and 7-9, the fiber tip fluid output device 14 comprises a generally cylindrical body having an outer surface, a proximal end, a distal end, and a lumen extending between the proximal end and the distal end. The lumen is sized and shaped to accommodate the fiber tip 51*a* therethrough so that the fiber tip 51*a* extends through the lumen from the proximal end to the distal end of the generally cylindrical body. The fiber tip fluid output device 14 further comprises a plurality of apertures 125 extending around the generally cylindrical body. Each of the apertures 125 fluidly connects the outer surface to the lumen. As presently embodied, the lumen comprises a first diameter near the proximal end and a second diameter near the distal end, wherein in the illustrated embodiment the second diameter is greater than or equal to about two times the first diameter. As presently embodied, the lumen comprises a proximal lumen section and a distal lumen section, the proximal lumen section having a diameter which in the illustrated embodiment is equal to the first diameter and the distal lumen section having a diameter which in the illustrated embodiment is equal to the second diameter. The proximal lumen section comprises a proximal end, a distal end, and a lumen axis extending between the proximal end and the distal end; the distal lumen section comprises a proximal end, a distal end, and a lumen axis extending between the proximal end and the distal end; and the diameter of the proximal lumen section in the illustrated embodiment can be substantially constant along a length of the proximal lumen section between the proximal end of the proximal lumen section and the distal end of the proximal lumen section. The diameter of the distal lumen section can be substantially constant along a length of the distal lumen section between the proximal end of the distal lumen section and the distal end of the distal lumen section. In the illustrated embodiment, the first diameter transitions to the second diameter at the distal end of the proximal lumen section and the proximal end of the distal lumen section, a distal opening of the fiber tip fluid output device 14 has a diameter which is equal to the second diameter, and a proximal opening of the fiber tip fluid output device 14 has a diameter which is equal to the first diameter. In the illustrated embodiment, each of the apertures 125 has a diameter which is about half of the first diameter.

The apertures 125 can be disposed within a first depression 121. A second depression extends around the generally cylindrical body near the proximal end, and a third depression extends around the generally cylindrical body near the distal end, wherein the first depression is disposed about half way between the second depression and the third depression in the illustrated embodiment. As presently embodied, the distal lumen section tapers into the proximal lumen section along a length of the lumen that in the illustrated embodiment is equal to about one third of at least one of the cross-sectional diameters of the apertures 125.

The rotating handpiece 10 of the illustrated embodiment can use the electromagnetically induced cutting system disclosed in U.S. Pat. No. 5,741,247, the entire contents of which are expressly incorporated herein by reference. For example, an engineered and controllable atomized distribution of fluid particles is placed into an interaction for absorption of electromagnetic radiation (from the fiber tip 51*a*) and for subsequent expansion to impart mechanical cutting forces onto a target or treatment surface. In the illustrated embodiment of FIG. 1, separate air and fluid lines 111, 113, which may be similar to those described in U.S. Pat. No. 5,741,247, run parallel to one another in the distal direction toward the feed channels 115, 117. In other embodiments, the air and fluid lines 111, 113 may comprise a first fluid line for carrying a first fluid and a second fluid line for carrying a second fluid, and further may comprise one or more additional fluid lines (not shown). Thus, while the illustrated embodiment describes the first fluid being air and the second fluid being water, the present disclosure is not limited to such structure and use. For example, the first and second fluids, and additional fluids, may comprise any of the components described in U.S. Pat. No. 5,785,521, the entire contents of which are expressly incorporated herein by reference. Some or all of the components of U.S. Pat. No. 5,785,521 may be premixed and carried through fluid lines, such as the lines 115, 117, or not premixed and mixed within the circumferential chamber 119 discussed below. The feed channels 115, 117, carrying a supply of air and water, respectively, as presently embodied, feed into circumferential chamber 119. Referring to FIGS. 5*a*-5*c*, the circumferential chamber 119 can be formed in a first depression 121 of the fiber tip ferrule 123. In an alternative embodiment, the section 121 may not have any depression.

As can be seen from FIG. 5*b*, for example, four apertures 125 are disposed in the first depression 121 of the fiber tip ferrule 123. In modified embodiments, other numbers of apertures may be incorporated. Air traveling into the circumferential chamber 119 from the feed channel 115, and water traveling into the circumferential chamber 119 from the feed channel 117, are both initially mixed in the circumferential chamber 119. In one embodiment, the first and second fluids may comprise air and a medicated or flavored water, and in another embodiment the first and second fluids may comprise water and at least one other fluid. In still another embodiment, at least one of the first and second fluids may comprise a medicament, such as chlorhexidine gluconate.

The initially-mixed air and water travel from the circumferential chamber 119 through the orifices 125 and into the lumen 133. The air and water is further mixed and atomized within the lumen 133. The atomized water under air pressure subsequently travels along the fiber tip 51 in a direction toward the output end 136 of the fiber tip 51. In a typical embodiment, the fiber tip 51*a* is permanently affixed to and extends through the fiber tip fluid output device 14. As presently embodied, three O-ring seals 139 are provided to seal the inside of the rotating handpiece from the air and water.

Figure 7:
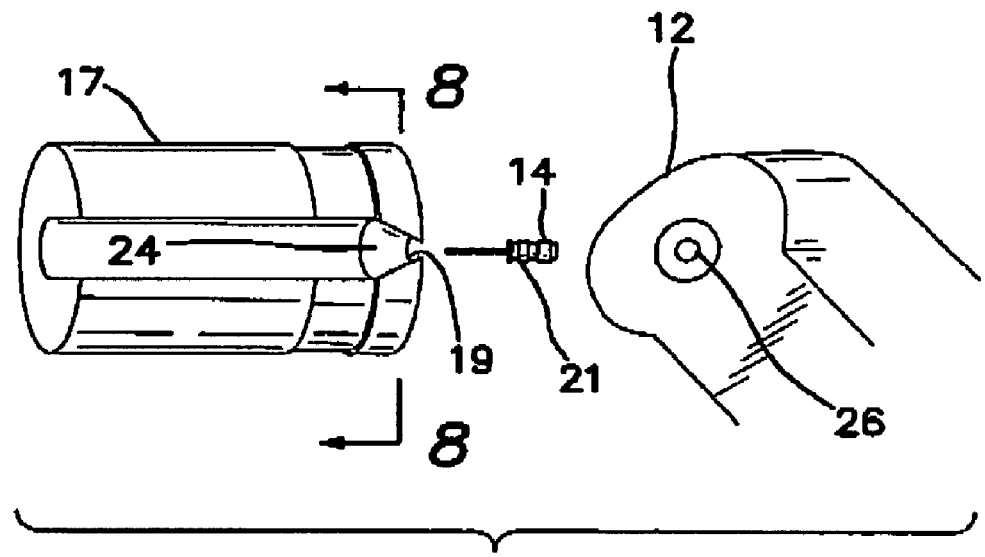
FIG. 7 is a perspective view of the loading tool, fiber tip fluid output device, and handpiece head in a disassembled configuration.
Figure 8:
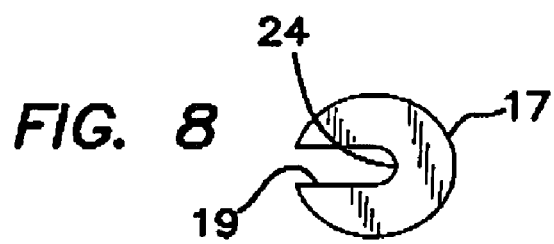
FIG. 8 is an end view of the loading tool, taken along the line 8-8 of FIG. 7.

FIG. 7 illustrates the loading tool 17, the fiber tip fluid output device 14, and handpiece head 12 in a disassembled configuration, and FIG. 8 is an end view of the loading tool 17, taken along the line 8-8 of FIG. 7.

Figure 9:
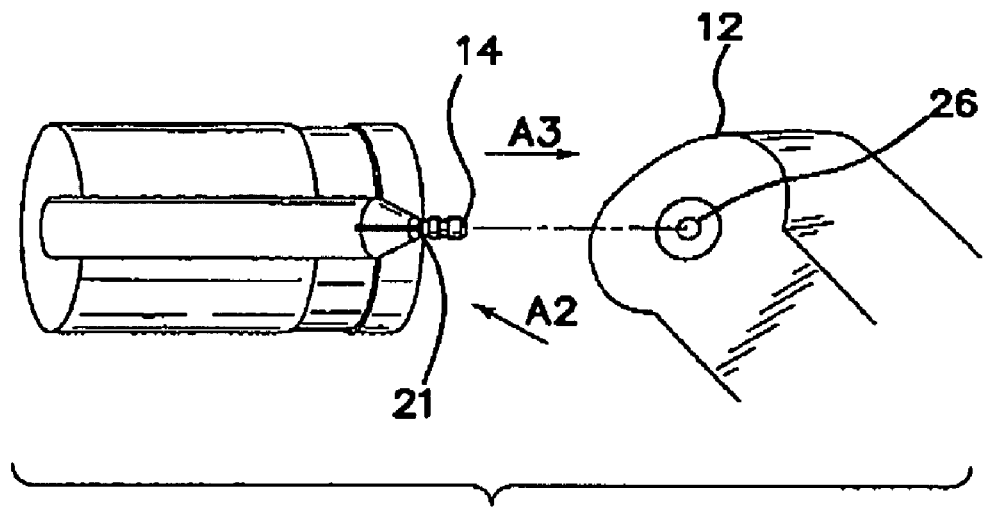
FIG. 9 is a perspective view of the fiber tip fluid output device partially secured onto the loading tool, just before insertion of the fiber tip fluid output device into the handpiece head.

FIG. 9 shows the fiber tip fluid output device 14 partially secured onto the loading tool 17. The proximal end of fiber tip fluid output device 14 can be gripped by the hand of a user and slid into the slot 19 of the loading tool 17 in the direction of the arrow A2. As presently embodied slot 19 fits around the third depression 21 of the fiber tip fluid output device 14, and the fiber tip fluid output device 14 is slid within the slot 19 in the direction of the arrow A2 until the fiber tip fluid output device 14 reaches the end 24 of the slot 19. The loading tool is then advanced in the direction of the arrow A3 to firmly secure the fiber tip fluid output device 14 into the orifice 26 of the handpiece head 12. The loading tool 17 is then removed from the fiber tip fluid output device 14 to leave the fiber tip fluid output device 14 firmly secured within the orifice 26. As presently embodied, a width of the slot 19 is slightly larger than a diameter of the third depression 21, so that the fiber tip fluid output device 21 can be removably and snugly held by the loading tool 17.

Figure 2:
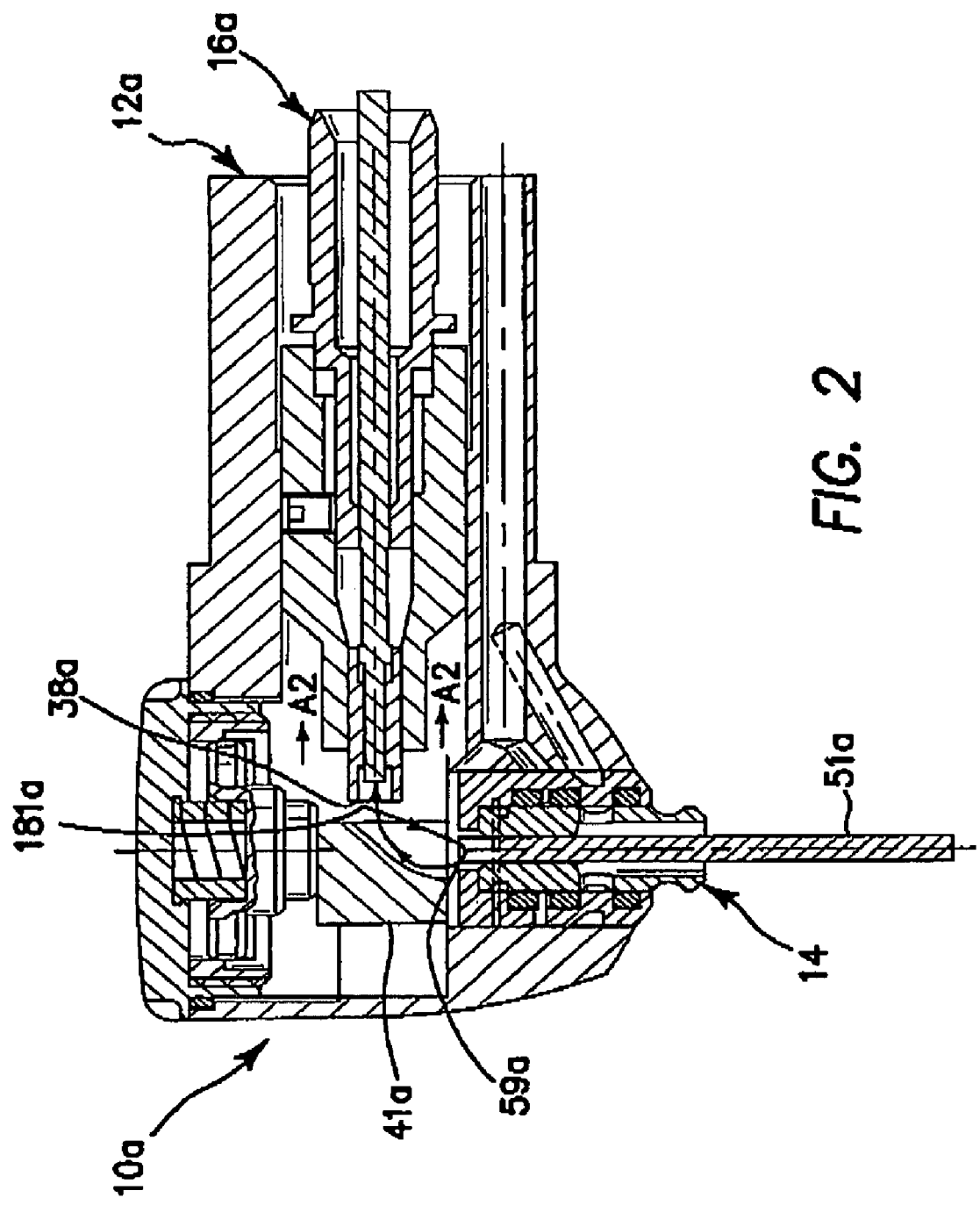
FIG. 2 is a cross-sectional view of an alternative embodiment of the rotating handpiece.

Referring to FIG. 3, the removable trunk fiber assembly 16 can be provided with three radial ports for introducing air, water, and (optionally) cooling air. More particularly, a fluid radial channel 161 feeds fluid (e.g., water) into the fluid channel 111, an air radial channel 163 feeds air into the air channel 113, and an optional cooling-air radial channel 165 feeds cooling air along a cooling-air channel, which exits in close proximity to the parabolic mirror 41. In a representative embodiment, the exit angle of the cooling air channel directs cooling air directly onto the parabolic mirror 41, so that the cooling air is reflected from the parabolic mirror 41 onto the input end 59 of the fiber tip 51 and, subsequently, onto the window 43. In FIG. 2, the cooling air exits from an orifice 181a and is channeled directly onto the input end 59a of the fiber tip 51a. Subsequently, the air is directed onto the parabolic mirror 41 and reflected onto the output end 55 of the trunk fiber optic 45. This configuration could also be implemented for the system of FIG. 1, wherein the cooling air subsequently is directed onto the window 43. Alternatively, in the embodiment of FIG. 2, the cooling air exiting the orifice 181a can be channeled directly onto the parabolic mirror 41, focusing onto the input end 59a of the fiber tip 51. In the embodiments of both FIG. 1 and FIG. 2, the cooling air is subsequently channeled in the direction of the arrows A2 through channels formed in the chuck 23. As shown in FIG. 3a, the chuck 23 can have portions of its two sides removed, to thereby form channels for passage of the cooling air. The cooling air travels through the channels of the chuck 23 under a vacuum pressure and, subsequently, is drawn into a removal port 191. Upon entering the removal port 191 under the vacuum, the cooling air travels in a direction opposite to the arrow A1 and exits the removal trunk fiber assembly 16. The four O-rings 196 insulate the radial channels 161, 163, 165 from one another.

Figure 6A:
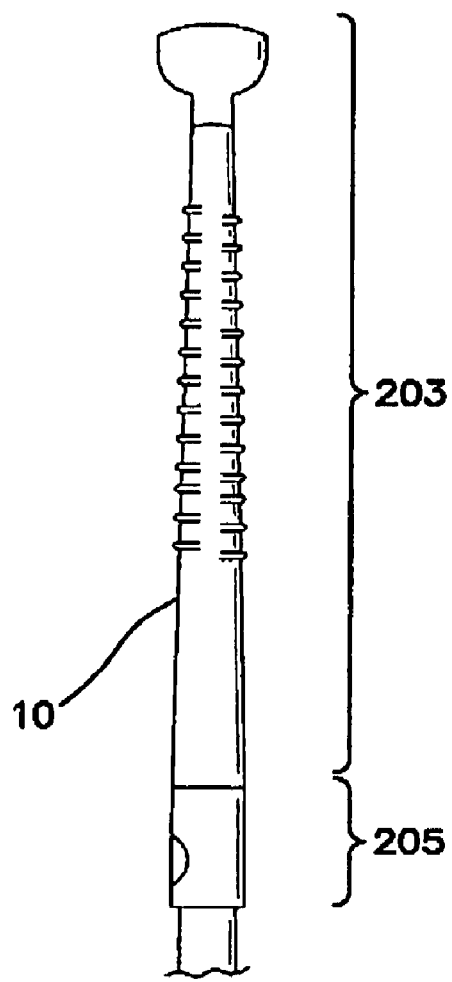
Figure 6B:
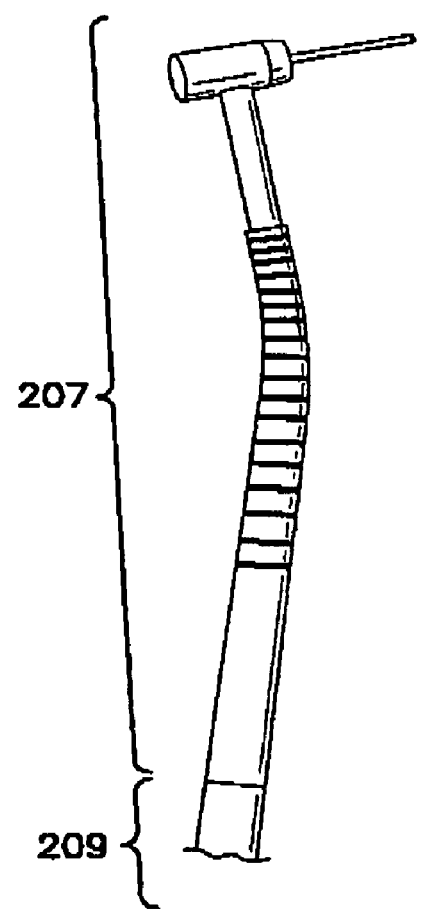

FIG. 6a illustrates a side elevation view of the assembled rotating handpiece 10 and FIG. 6b illustrates a modified embodiment of the rotating handpiece 10, wherein the neck is slightly bent. In FIG. 6a the portion indicated by reference numeral 203 is adapted to rotate about an axis of the rotating handpiece 10. The portion 205 does not rotate. Similarly, in FIG. 6b, the portion 207 is adapted to rotate about an axis of the rotating handpiece, and the portion 209 does not rotate. In the embodiment of FIG. 6b, the trunk fiber optic is configured to be slightly flexible, since the trunk fiber optic will need to bend and flex as the portion 207 is rotated relative to the portion 209. In either of the embodiments of FIGS. 6a and 6b, the user holds the rotating portion (203 or 207) with his or her thumb and two fingers (such as is conventional in the art) and allows the stationary portion (205 or 209) to rest on a portion of the hand bridging the user's forefinger and thumb. The three fingers holding the rotating portion (203 or 207) contact the rotating portion and can rotate the rotating portion, as the fixed portion (205 or 209) does not rotate and rests on the portion of the hand bridging the hand and the forefinger.

The following figures show exemplary embodiments of radiation emitting apparatuses which are constructed to emit electromagnetic radiation in non-centered or non-concentrically focused manners, relative to the output from a cylindrically-shaped fiber optic end (i.e., a truncated fiber end), onto target surfaces or treatment sites. The target surface or treatment site can comprise, for example, a part of the body, such as a tooth, a knee, a wrist, or a portion of the jaw to be treated.

The output radiation can be engineered to have a spatial energy distribution which differs from the spatial energy distribution of a conventional truncated fiber end. More particularly, in accordance with an aspect of the present invention, a radiation emitting apparatus is constructed to generate output radiation having a spatial energy distribution with one or more energy concentrations or peaks located in areas other than a center of the spatial energy distribution. A component of the output radiation not aligned along a fiber optic axis can be greater than a component aligned along the fiber optic axis. The center of the spatial energy distribution can be defined as an area aligned with (or intersecting) an optical fiber axis of the shaped fiber optic tip or an area aligned with (or intersecting) an average direction of propagation of the output radiation. According to one aspect, the center of the spatial energy distribution can be defined as a central part of a cross-section of the output radiation taken in a direction orthogonal to the direction of propagation of the output radiation.

Figure 10A:
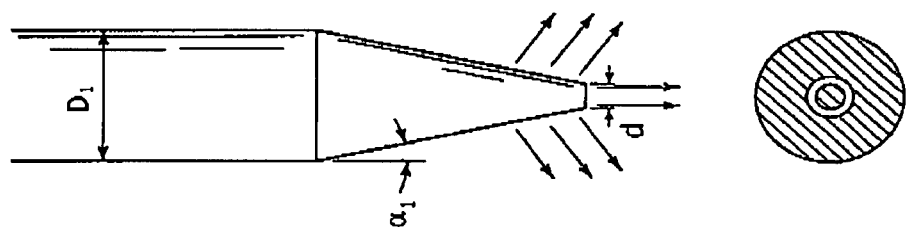
FIGS. 10A and 10B are cross-sectional views of shaped fiber optic tips having conical side-firing output ends in accordance with certain embodiments of the present invention.
Figure 10B:
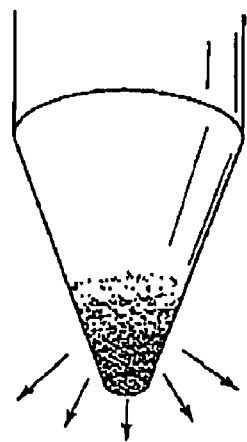

With particular reference to FIGS. 10A and 10B, a cross-sectional view of a shaped fiber optic tip comprising a conical side-firing output end in accordance with an embodiment of the present invention is shown. The side-firing output end is depicted comprising a conical shape that tapers in an output direction of propagation of electromagnetic radiation. In a typical embodiment, the side-firing output end is polished to a symmetric, or substantially symmetric, conical shape to, for example, attenuate or avoid undesirable phenomena such as masking and power losses. For example, the shaped fiber optic tip may be grasped and moved to position a distal end thereof onto an operative surface of a polishing machine. The distal end of the shaped fiber optic is then oriented with respect to the operative surface, and rotated at a steady rate to remove portions of the fiber in an even fashion about the fiber optic axis, to thereby polish the distal end of the shaped fiber optic tip into a conical side-firing output end. The shaped fiber optic tip may comprise, for example, sapphire, diamond, or quartz (glass), and portions of the tip may be "frosted" to provide for different types of light diffusion (e.g., scattering) effects.

In accordance with an aspect of the present invention, a percentage of beams of laser radiation can exit from the side-firing output end at relatively high angles (e.g., up to 90 degrees) with respect to the fiber optic axis and can travel distally and radially away from the fiber optic axis. The beams can form a ring-shaped pattern, and a percentage of beams of laser radiation can exit along the optical axis of the fiber to form a centrally illuminated spot. A dark "blind spot" is formed in front of the side-firing output end such that the output beam pattern or illuminated area comprises a non-illuminated portion between the ring and the spot.

In accordance with an aspect of the present invention, the side-firing output ends described herein may be used for caries removal from predetermined locations (e.g., side walls) of tooth cavities. Using the side-firing output ends of the present invention, undercuts may be effectively generated in caries procedures wherein each undercut may comprise a removed volume of caries defining a reverse-mushroom shaped aperture in the tooth which has a size at the surface of the tooth that is less than sizes of the aperture beneath the surface and which is to be filled with amalgam. Sizes of the aperture of such an undercut may progressively increase with distance away from the tooth surface in a direction toward a center of the tooth. For example, a dentist may insert a curved stainless steel probe into a cavity, detect caries material on a surface (e.g., sidewall) of the cavity, remove the curved stainless steel probe, insert a shaped fiber optic tip of the present invention having a side-firing output end into the cavity, position the side-firing output end to ablate the detected caries material, activate a laser to remove the detected caries material, and then (optionally) repeat the process until all detectable or a desired level of caries material has been removed. The shaped fiber optic tips of the present invention, and in particular their side-firing output ends, can thus facilitate generation of reverse-mushroom shaped apertures by way of operation of their side-firing characteristics, which can facilitate, for example, removal of tissue (e.g., caries) from side walls of the cavity down beneath the surface of the tooth.

In FIG. 10A, the angle $\alpha_1$ can range from about 10 to about 30 degrees; the diameter D1 can range from about 0.8 to about 1.2 mm; and the diameter d can be about 100 um.

Figure 11:
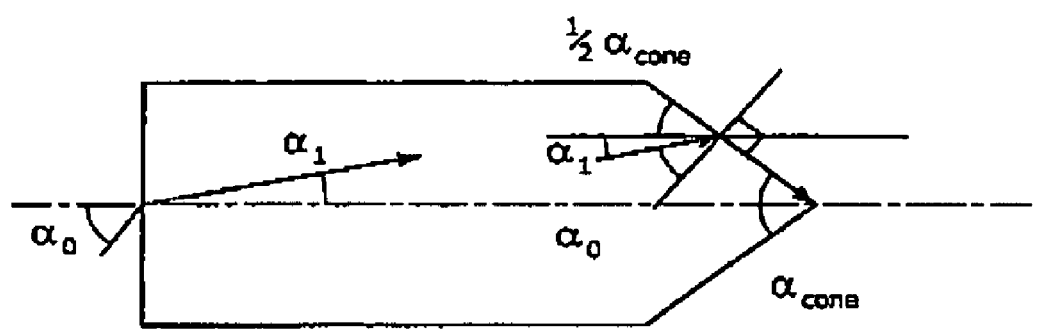
FIG. 11 shows calculation considerations pertaining to determination of a cone angle of a fiber optic end of a radiation emitting apparatus.

In accordance with another aspect of the present invention, dimensions of the side-firing output ends of the shaped fiber optic tips can be selected to obtain internal reflection within the shaped fiber optic tip at, for example, the tip/air interface, as elucidated for example in FIG. 11. With reference to this figure in the context of a conically-shaped, side-firing output end, the full angle (i.e., total cone angle) at a distal region of the side-firing output end (e.g., cone) can be in the range from 10 degrees to 170 degrees, and in particular examples between 50 degrees and 100 degrees. The shaped fiber optic tip can be a single fiber optic or in modified embodiments a bundle or fused bundle. Generally, the shaped fiber optic tip can have a diameter between 50 and 2000 microns, or in other embodiments between 400 and 2000 microns, and can have a numerical aperture (N.A.) depending on the material. The exemplary shaped fiber optic tip can be made of silica or other materials, such as sapphire, or other materials disclosed in U.S. Pat. No. 5,741,247, the entire contents of which are incorporate by reference herein, and can also comprise a hollow waveguide in modified embodiments. In the exemplary embodiment of FIG. 11, the shaped fiber optic tip comprises a 600 micron core diameter, a numerical aperture of 0.39, an acceptance angle, $\alpha_1$, of 15.6 degrees, and a full cone angle of 60 degrees to 62 degrees.

The full cone angle can be determined using, for example, Snell's Law of Refraction, $n_o \sin(\alpha_o) = n_1 \sin(\alpha_1)$, for all waveguide modes to experience total internal reflection on at least one of the tapered surfaces of the side-firing output end before exiting through the side-firing output end. More particularly, in the illustration of FIG. 11, the cone comprises a first tapered surface (shown near top of drawing page) and an opposing second tapered surface (shown near bottom of drawing page). According to an implementation of the present invention in which internal reflection occurs, light striking the first tapered surface is reflected toward and exits through the second tapered surface to thereby achieve a side-firing effect.

In the illustration, the refractive indices $n_0$ and $n_1$ can be 1.0 and 1.45, respectively, corresponding to an implementation of a quartz conical side-firing output end transmitting into air, and further values may be implemented wherein $\alpha_o=8.0$ degrees and $\alpha_1=5.5$ degrees. Beginning with an equation that $(\frac{1}{2})\alpha_{cone+\alpha 1} + \alpha_{t.r.} = 90$ degrees, wherein $\alpha_{cone}$ is defined as the total cone angle and $\alpha_{t.r.}$ is defined as the angle for total internal reflection, the angle for total internal reflection, $\alpha_{t.r.}$, can be isolated to yield $\alpha_{t.r.} = \sin^{-1}(n_o/n_1)$ which in the present example equals 43.6 degrees. When $(\frac{1}{2})\alpha_{cone}=40.9$ degrees, the total cone angle can be determined in the example as $\alpha_{cone}=81.8$ degrees.

Although the full cone angle in the illustrated embodiment of a cone is selected to facilitate a large degree, or total, internal reflection, modified embodiments of cones (e.g., having other shapes or materials) or other side-firing output ends may be constructed wherein the internal reflection (i.e., reflection off of a first surface or first tapered surface, or the percentage of reflection from light first striking any tapered or other surface of the side-firing output end) is about 50% or greater. In still other embodiments, a total angle can be constructed to provide for an internal reflection of at least 25%. In further embodiments, however, other varying amounts of internal reflection can be implemented.

Figure 12A:
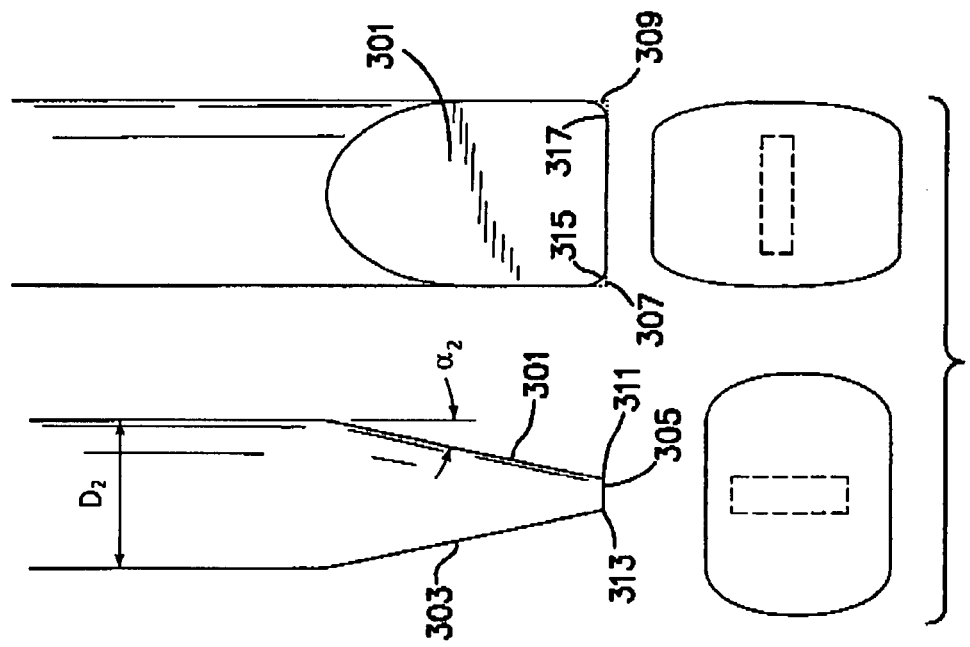
FIGS. 12A and 12B are views of a side firing tip comprising a shaped fiber optic tip having dual bevel-cut side-firing output ends according to an embodiment of the present invention.
Figure 12B:
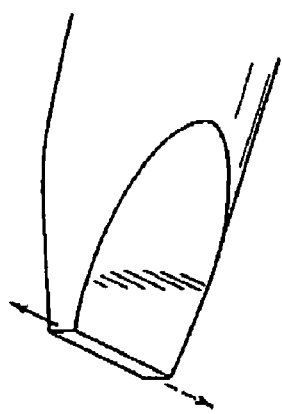

In an embodiment wherein the shaped fiber optic tip is formed of quartz or sapphire, the shaped fiber optic tip may have diameters suitable for, in certain applications, root canal procedures. FIGS. 12A and 12B are views of a side firing tip comprising a shaped fiber optic tip having dual bevel-cut side-firing output ends according to a modified embodiment of the present invention, wherein bevel cuts 301 and 303 taper in an output direction of propagation of electromagnetic radiation to provide a capability of directing light distally and radially away from the fiber optic axis as with the above-described and other herein-described tapered surface embodiments. In a typical embodiment, the side-firing output end comprises a material such as sapphire, diamond or quartz that is polished to a bevel-cut shape. For example, the shaped fiber optic tip may be grasped and moved to position a distal end thereof onto an operative surface of a polishing machine, with the distal end of the shaped fiber optic being oriented with respect to the operative surface, and not rotated, to remove portions of and polish a side 301 of the distal end of the shaped fiber optic tip into a bevel-cut side-firing output end. The side 301 can be formed, for example, to have an angle $\alpha_2$, measured between the optical axis of the fiber optic tip and the surface of side 301, ranging from about 5 to about 10 degrees.

The shaped fiber optic tip then may, optionally, be rotated 180 degrees, or another angle in modified embodiments, and the procedure can be repeated, in whole, in part, to the same, to a greater, or to a lesser degree, to remove the same, similar, or dissimilar portions of and polish a side 303 of the distal end of the shaped fiber optic tip, thereby yielding a structure with two output-modified (e.g., flattened) sides 301 and 303 that taper to a truncated point 305. The side 303 can be formed, for example, to have an angle $\alpha_2$, measured between the optical axis of the fiber optic tip and the surface of side 303, ranging from about 5 to about 10 degrees. The sides (e.g., sides 301 and 303) may be oppositely disposed to provide a capability of directing light distally and in opposing directions or disposed at non-opposing positions (e.g., at angles other than 180 degrees), and/or may number in two as illustrated or fewer or greater, and/or may be worked to the same shape and/or the same amount removed as illustrated and/or different shapes or amounts removed. The resulting shape, or blade, as illustrated on the left-hand side of FIG. 12A, may be compared to the shape of a flat-head screw driver. The dimension "d" defined in FIG. 10A as having a value from about 100 um may be implemented, for example, in the FIG. 12A embodiment. In particular constructions, the dimension "d"_ (not labeled) in FIG. 12A can range from about 100 um to about 150 um.

Subsequently, turning to the depiction on the right-hand side of FIG. 12A, which is rotated 90 degrees with respect to the left-hand depiction of the same figure, a first corner 307 and/or a second corner 309, both shown in phantom, of the blade may be modified (e.g., rounded).

In the illustrated embodiment, the corners 307 and 309 are rounded only at opposing ends of the distal end of the blade; in other words, the edges 311 and 313 shown in the depiction on the left side of FIG. 12A are not rounded in the illustrated example. The rounding can be performed using the same polishing machine referenced above.

For example, following the above-described polishing procedure, the shaped fiber optic tip may be grasped and moved to position a distal end thereof onto an operative surface of a polishing machine, with the distal end of the shaped fiber optic being oriented with respect to the operative surface, and rotated, to remove portions of and polish the first corner 307 of the distal end of the shaped fiber optic tip. The resulting first curved surface 315 may be formed to have a regular or irregular curvature and/or may be formed to have a partially-curved, partially-straight construction or, as illustrated, a curved construction that comprises a relatively regular curvature. The first curved surface 315 can be formed, in accordance with certain exemplary embodiments, to have a radius of curvature ranging from about 200 to 500 um.

Following formation of the first curved surface 315, a related, substantially similar, or substantially identical process may, optionally, be implemented to form a second curved surface 317. The second curved surface 317 may have one or more similar or dissimilar characteristics with respect to the first curved surface 315. In the illustrated example, the second curved surface 317 is formed to be substantially symmetrical with the first curved surface 315.

An embodiment comprising only a single bevel cut may comprise a shape identical or similar to that shown on the left-hand side of FIG. 12A, with the side 301 formed but without the side 303 formed, wherein the distance "d" can be greater, such as from about 475 um to about 800 um. Alternatively, such a single-sided embodiment may comprise a greater angle $\alpha_2$, or may comprise a much longer side (e.g., side 303), so that the distance "d" is held within a range from about 100 um to about 150 um. In any such embodiment or implementation comprising only a single bevel cut, the shape may be identical or similar to the right-hand side depiction of FIG. 12A, with one or both of the first curved surface 315 and the second curved surface 317 being formed.

Figure 13B:
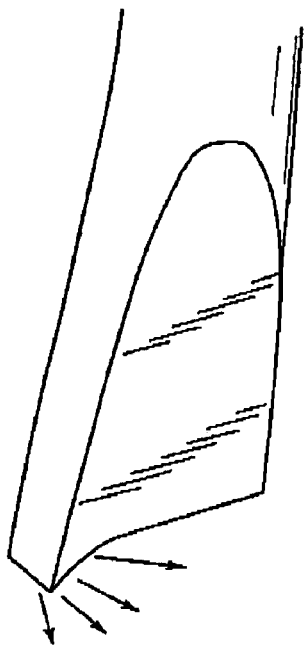
FIGS. 13A and 13B are views of a side firing tip comprising a shaped fiber optic tip having dual bevel-cut side-firing output ends with an arched shape according to another embodiment of the present invention.
Figure 13A:
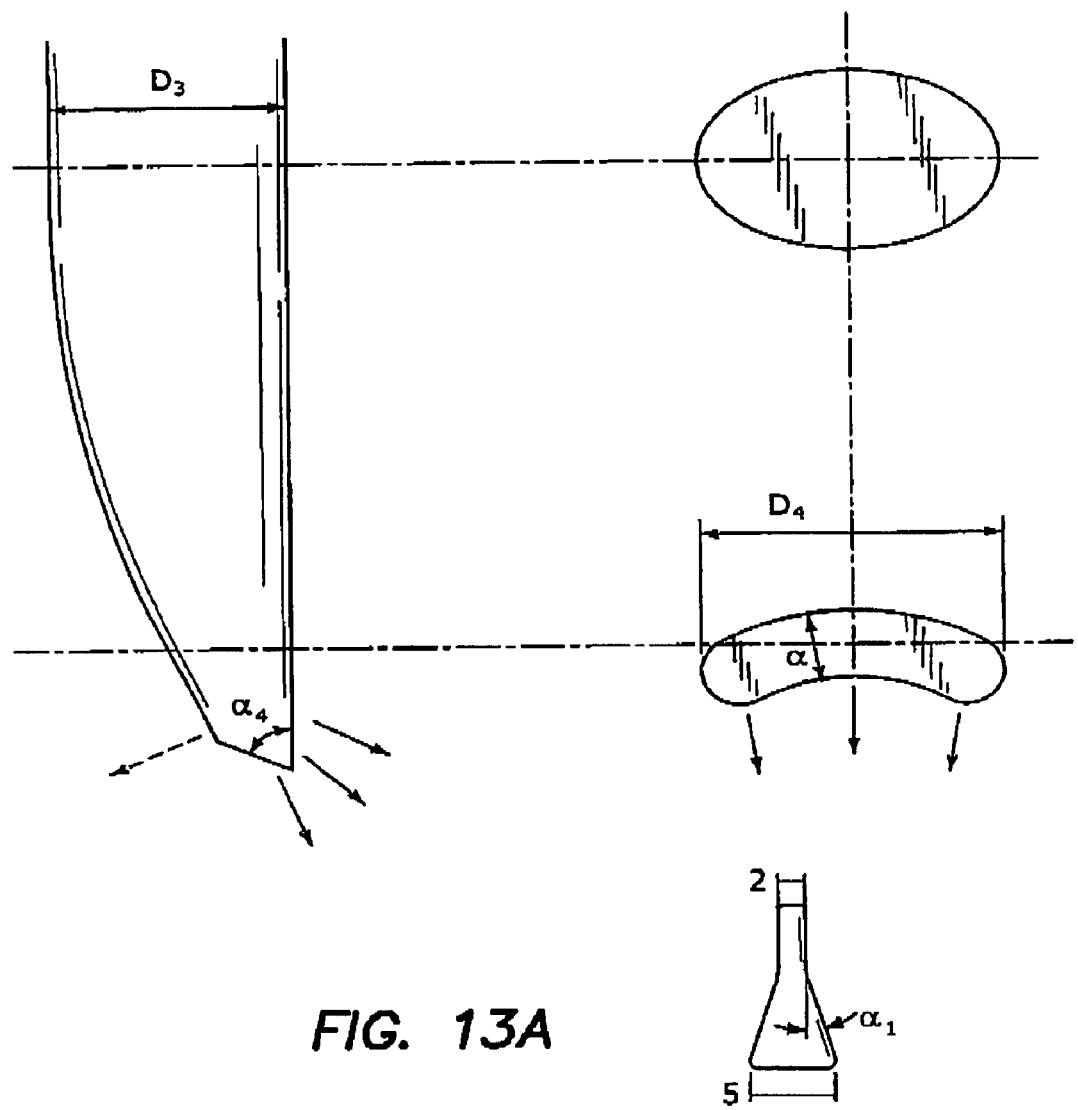

Dimensions of the side-firing output ends of the shaped fiber optic tips can be selected to obtain total, substantial or a large degree of internal reflection of electromagnetic radiation at one side and firing through the opposite bevel-cut side of the side-firing output end of the shaped fiber optic tip. Another embodiment of a side firing tip is elucidated in FIGS. 13A and 13B.

Regarding the side-firing output ends of the shaped fiber optic tips of FIGS. 10A, 10B, 12A, 12B, 13A and 13B, any of these output ends may be modified or otherwise formed to have non-cylindrical, non-symmetrical, or otherwise irregular or different shapes, such as spherical, chiseled, or other light-intensity altering (e.g., dispersing) shapes and or surface (s), in additional embodiments.

Also, regarding the side-firing output ends of the shaped fiber optic tips, any of these output ends further can be modified by removing more or less of the parts of the distally-disposed output ends to yield, for example, more or less truncated-cone or truncated-bevel distal ends that provide end-firing components. Any of these tips and output ends may be modified or otherwise formed to have hollow interiors defining central fluid-delivery paths such as those described in connection with FIGS. 14a and 14b, and/or operated as such in whole or in part as described in connection with FIGS. 14a and 14b of the co-pending application referenced in the first paragraph of this disclosure. In exemplary implementations, the hollow interiors may be centered along fiber optic axes of the shaped fiber optic tips and/or may be aligned with what would otherwise be the planar output surfaces so that the planar output surfaces are not surfaces but rather are output openings of the hollow interiors.

In other implementations, the modified output ends (e.g., planar output surfaces) may have other orientations which are not perpendicular to the optical axes of the fiber optics, and in still further implementations the modified ends may comprise curved, rounded, or other non-planar surfaces, which may be wholly or partially frosted or otherwise etched.

The modified output ends (e.g., planar output surfaces) can generate output beam patterns similar to those described herein but with more or less filled center portions as a result of laser energy passing through, unrefracted, the planar output surfaces. The shapes and intensities of the filled center portions in the output beam patterns, resulting from implementations of the modified output ends, can be changed by changing characteristics (e.g., diameter and/or surface characteristics) as will be recognized by one skilled in the art in light of this disclosure.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

What is claimed is:

1. A laser handpiece, comprising a shaped fiber optic tip having a proximal end, a distal end, an optical axis extending therebetween, and a side-firing output end with at least one beveled output oriented to direct light distally and radially away from the axis, the at least one beveled output comprising a planar surface with a distal edge having at least one rounded corner with a radius of curvature greater than about 200 microns, wherein a spatial distribution of electromagnetic radiation emitted from the side-firing output end has a component not aligned along the optical axis that is greater than a component aligned along the optical axis.

2. The laser handpiece as set forth in claim 1, wherein the distal edge comprises two rounded corners.

3. The laser handpiece as set forth in claim 1, the side-firing output end having two beveled outputs oriented to direct light distally and radially away from the axis.

4. The laser handpiece as set forth in claim 3, each of the two beveled outputs comprising a planar surface with a distal edge having at least one rounded corner.

5. The laser handpiece as set forth in claim 4, each distal edge having two rounded corners.

6. The laser handpiece as set forth in claim 4, the planar surfaces being oriented to direct light distally and in opposing radial directions.

7. The laser handpiece as set forth in claim 6, each distal edge having two rounded corners.

8. The laser handpiece as set forth in claim 1, further comprising a source of positive pressure coupled to the shaped fiber optic tip.

9. The laser handpiece as set forth in claim 8, the source of positive pressure being coupled to deliver fluid along a path, which is substantially parallel to the optical axis, to the shaped fiber optic tip.

10. The laser handpiece as set forth in claim 9, wherein the source of positive pressure and the path are configured to deliver the fluid to a vicinity of the shaped fiber optic tip as atomized fluid particles.

11. The laser handpiece as set forth in claim 10, wherein the source of positive pressure and the path are structured to place the atomized fluid particles into a volume in close proximity to the side-firing output end; and
the laser handpiece is constructed to deliver electromagnetic energy from an electromagnetic energy source into the atomized fluid particles in the volume to thereby expand the atomized fluid particles in such a way that when the volume is placed next to a target surface disruptive forces are imparted onto the target surface.

12. The laser handpiece as set forth in claim 11, wherein the fluid particles comprise water.

13. The laser handpiece as set forth in claim 12, wherein the target surface comprises tooth tissue.

14. The laser handpiece as set forth in claim 12, wherein the electromagnetic energy source comprises one of a wavelength within a range from about 2.69 to about 2.80 microns and a wavelength of about 2.94 microns.

15. A laser handpiece, comprising a shaped fiber optic tip having a proximal end, a distal end, an optical axis extending therebetween, and a side-firing output end with at least one beveled output oriented to direct light distally and radially away from the axis, the at least one beveled output comprising a planar surface with a distal edge having at least one rounded corner, wherein a spatial distribution of electromagnetic radiation emitted from the side-firing output end has a component not aligned along the optical axis that is greater than a component aligned along the optical axis, wherein a radius of curvature of the at least one rounded corner ranges from about 200 to about 500 um.

16. A laser handpiece, comprising a shaped fiber optic tip having a proximal end, a distal end, an optical axis extending therebetween, and a side-firing output end with at least one beveled output oriented to direct light distally and radially away from the axis, the at least one beveled output comprising a planar surface with a distal edge having at least one rounded corner, wherein a spatial distribution of electromagnetic radiation emitted from the side-firing output end has a component not aligned along the optical axis that is greater than a component aligned along the optical axis, wherein: the distal edge comprises two rounded corners; and a radius of curvature of each of the rounded corners ranges from about 200 to about 500 um.

17. A laser handpiece, comprising a shaped fiber optic tip having a proximal end, a distal end, an optical axis extending therebetween, and a side-firing output end with at least one beveled output oriented to direct light distally and radially away from the axis, the at least one beveled output comprising a planar surface forming an angle of about 5 to about 30 degrees with the optical axis and having a distal edge with at least one rounded corner defined by a radius of curvature greater than about 200 microns, wherein a spatial distribution of electromagnetic radiation emitted from the side-firing output end has a component not aligned along the optical axis that is greater than a component aligned along the optical axis.

18. The laser handpiece as set forth in claim 17, wherein:
the planar surface forms an angle of about 5 to about 10 degrees with the optical axis; and
the planar surface comprises a distal edge which comprises two rounded corners.

19. The laser handpiece as set forth in claim 17, wherein:
the planar surface forms an angle of about 5 to about 10 degrees with the optical axis; and
the side-firing output end comprises two beveled outputs oriented to direct light distally and radially away from the axis.

20. The laser handpiece as set forth in claim 19, each of the two beveled outputs comprising a planar surface with a distal edge having at least one rounded corner.

21. The laser handpiece as set forth in claim 20, each distal edge having two rounded corners.

22. The laser handpiece as set forth in claim 20, the planar surfaces being oriented to direct light distally and in opposing radial directions.

23. The laser handpiece as set forth in claim 22, each distal edge having two rounded corners.

24. The laser handpiece as set forth in claim 17, the planar surface forming an angle of about 5 to about 10 degrees with the optical axis, and the laser handpiece further comprising a source of positive pressure coupled to the shaped fiber optic tip.

25. The laser handpiece as set forth in claim 24, the source of positive pressure being coupled to deliver fluid along a path, which is substantially parallel to the optical axis, to the shaped fiber optic tip.

26. The laser handpiece as set forth in claim 25, wherein the source of positive pressure and the path are configured to deliver the fluid to a vicinity of the shaped fiber optic tip as atomized fluid particles.

27. The laser handpiece as set forth in claim 26, wherein the source of positive pressure and the path are structured to place the atomized fluid particles into a volume in close proximity to the side-firing output end; and
the laser handpiece is constructed to deliver electromagnetic energy from an electromagnetic energy source into the atomized fluid particles in the volume to thereby expand the atomized fluid particles in such a way that when the volume is placed next to a target surface disruptive forces are imparted onto the target surface.

28. The laser handpiece as set forth in claim 27, wherein the fluid particles comprise water.

29. The laser handpiece as set forth in claim 28, wherein the target surface comprises tooth tissue.

30. The laser handpiece as set forth in claim 28, wherein the electromagnetic energy source comprises one of a wavelength within a range from about 2.69 to about 2.80 microns and a wavelength of about 2.94 microns.

31. The laser handpiece as set forth in claim 17, wherein the planar surface forms an angle of about 10 to about 30 degrees with the optical axis.

32. A laser handpiece, comprising a shaped fiber optic tip having a proximal end, a distal end, an optical axis extending therebetween, and a side-firing output end with at least one beveled output oriented to direct light distally and radially away from the axis, the at least one beveled output comprising a planar surface that forms an angle of about 5 to about 30 degrees with the optical axis, wherein a spatial distribution of electromagnetic radiation emitted from the side-firing output end has a component not aligned along the optical axis that is greater than a component aligned along the optical axis, wherein: the planar surface forms an angle of about 5 to about 10 degrees with the optical axis; the planar surface comprises a distal edge having at least one rounded corner; and a radius of curvature of the at least one rounded corner ranges from about 200 to about 500 um.

33. A laser handpiece, comprising a shaped fiber optic tip having a proximal end, a distal end, an optical axis extending therebetween, and a side-firing output end with at least one beveled output oriented to direct light distally and radially away from the axis, the at least one beveled output comprising a planar surface that forms an angle of about 5 to about 30 degrees with the optical axis, wherein a spatial distribution of electromagnetic radiation emitted from the side-firing output end has a component not aligned along the optical axis that is greater than a component aligned along the optical axis, wherein: the planar surface forms an angle of about 5 to about 10 degrees with the optical axis; the planar surface comprises a distal edge having two rounded corners; and a radius of curvature of each of the rounded corners ranges from about 200 to about 500 um.

* * * * *